United States Patent [19]

Berta

[11] Patent Number: 5,228,916
[45] Date of Patent: Jul. 20, 1993

[54] APPARATUS FOR CREATING A GELATIN COATING

[75] Inventor: Norbert I. Berta, Devon, Pa.

[73] Assignee: McNeil-PPC, Inc., Milltown, N.J.

[21] Appl. No.: 609,482

[22] Filed: Nov. 5, 1990

[51] Int. Cl.$^5$ .......................... B05C 1/02; B05C 3/18; B05C 3/20

[52] U.S. Cl. ........................ 118/30; 118/20; 118/233; 118/244; 118/258; 118/425; 118/426; 118/500; 118/58; 118/620; 118/206

[58] Field of Search .................. 118/18, 20, 30, 58, 118/233, 244, 258, 425, 426, 500, 620, 206; 427/3

[56] References Cited

U.S. PATENT DOCUMENTS

| | | | |
|---|---|---|---|
| 3,896,762 | 7/1975 | Banker | 118/30 |
| 4,532,881 | 8/1985 | Sakashita et al. | 118/30 |
| 4,867,983 | 9/1989 | Berta | 118/30 |
| 4,921,108 | 5/1990 | Berta | 209/625 |
| 4,940,499 | 7/1990 | Lebrun et al. | 427/3 |
| 4,965,089 | 10/1990 | Sauter et al. | 118/30 |
| 4,966,771 | 10/1990 | Berta | 118/16 |

FOREIGN PATENT DOCUMENTS 2434803 2/1975 Fed. Rep. of Germany ........ 118/30

Primary Examiner—W. Gary Jones
Assistant Examiner—Todd J. Burns
Attorney, Agent, or Firm—Joseph F. Shirtz

[57] ABSTRACT

Methods and apparatus for applying coating to products such as medicaments are disclosed. The present invention provides a apparatus comprising product holders and plates which interact with vacuum tubes to retain the product being coated in place while inverted and dipped into a tank of coating material. The vacuum tubes may be designed to hold product of nearly any shape or in any orientation. In a preferred embodiment, methods and apparatus for creating a two-color gelatin coating on a tablet are disclosed. In certain embodiments, additional apparatus are provided whereby the vacuum tubes rotate about their longitudinal axes and are placed in contact with a coating applicator, thereby applying a band or stripe of a coating material to a specified section of the product.

20 Claims, 5 Drawing Sheets

APPARATUS FOR CREATING A GELATIN COATING

The present invention relates to methods and apparatus for forming a coating on a product and, more particularly, to methods and apparatus for forming a coating comprised of a gelatinous substance on a tablet.

The present invention is related to my prior patents U.S. Pat. Nos. 4,921,108 issued on May 1, 1990; 4,867,983 issued on Sep. 19, 1989; and 4,820,524 issued on Apr. 11, 1989 and my U.S. patent application 190,551 filed on May 5, 1988 now U.S. Pat. No. 4,966,771 scheduled to issue on Oct. 30, 1990, all of which are assigned to the assignee of the present application and incorporated by reference as if fully set forth herein.

BACKGROUND OF THE INVENTION

Many products, from prescription drugs to commonly available vitamin tablets to candy, are manufactured in a form which may be described as a "tablet." The primary function of a tablet is to provide a single dose or "serving" of the product in a manner which is convenient to manufacture, package and consume. As pointed out in my previous patents and applications, referenced above, it has been found that certain individuals suffer from physiological and psychological problems which impede their ability to swallow tablets. It has also been found that by providing tablets with a smooth coating, such as a coating comprised of gelatin or a gelatinous substance that the "swallowability" of a tablet is greatly enhanced. Such coatings and the general considerations involved in their application, such as preparation and drying time, are well known to those of ordinary skill.

In addition to enhanced swallowability, there are numerous other reasons that it is desirable to provide a coating on a tablet. Such coatings protect the underlying product from deterioration and also serve to permit identifying colors or markings to be incorporated onto the design of the product, promoting product differentiation and brand identification. As pointed out in my previous patents and applications, it is also desirable in some instances to overlap two or more coatings to form a seam, thereby simulating the appearance of a hard gelatin capsule while providing a coated, solid (and thus tamper resistant) product.

Methods and apparatus for applying a gelatinous coating or other coating to a product which is in the form of a tablet are well known to those of ordinary skill. Such methods may include pan dipping or vacuum spraying of the coating material on to the tablet. Such methods are crude, however, producing uneven coatings which are generally unacceptable for commercial use. In an effort to improve the state of the art, the inventions disclosed by my previous patents and applications have provided methods and apparatus whereby individual products are held partially within a sleeve or "collet" and the exposed portion of the product precisely lowered into a dipping tank. As disclosed, bars or plates containing a plurality of product to be dipped are conveyed and rotated and the product itself is manipulated to provide even coatings of high quality and consistency at high volume. These inventions, however, do not permit every type of product such as certain styles of tablets and medicaments to be coated—or at least to be coated in a particular manner. For example, dipping the circular face of a substantially cylindrical tablet whose height is relatively small compared to its diameter would be difficult using the apparatus disclosed by my prior patents and applications, particularly if a circumferential seam is desired. Other examples include the difficulty of coating either a fragile product or applying fragile coating compositions. It has been found that certain coatings will be marred by the friction fit within the collets or similar retaining devices making these unsuitable for use in the apparatus of my prior inventions.

It is known to transport individual tablets or capsules through an immersion coating bath by retaining the tablets on individual vacuum tubes. For example, U.S. Pat. No. 3,896,762—Banker discloses a rotary coating apparatus for pharmaceutical solid dosage forms. Since the surface of the coating is horizontal it is tangential to the path of the tablet; accordingly, Banker discloses that it is necessary to rotate the vacuum tube holding the tablet around its longitudinal axis to achieve an even coating. There are, however, a number of practical shortcomings in the apparatus disclosed. First, although a dryer and ejector are disclosed, the overall system does not lend itself to high volume production or provide for modifications in drying time or inspection, etc. Secondly, the system disclosed by Banker is directed to passing one-half or more of the total depth dimension of the tablet through the coating solution. The tablet is then randomly ejected, with no provision being made to align or otherwise control the orientation of the tablet and the uncoated portion, if any, which exists. Moreover, there is no provision for adjusting the coating to achieve multi-colored or capsule-like coated products. Therefore, one of ordinary skill will appreciate that the system disclosed by Banker is of limited use in current manufacturing environments, where high volume and flexibility are important, along with the need for consistency and high quality.

Therefore, there exists a need for methods and apparatus which can consistently place a precisely defined amount of coating material on an individual product. Such methods and apparatus should be capable of producing coated products at high volume and should possess inherent flexibility to permit new designs and types of coatings to be incorporated without an undue degree of retooling.

It is therefore an object of the present invention to provide methods and apparatus for placing a coating on individual products such as medicinal tablets.

A further object of the present invention is to place such coatings upon the products in a variable manner, permitting one-half, or more or less than one-half of the surface area of the product to be coated with one or more coatings.

It is another object of the present invention to provide methods and apparatus for coating a product whereby the product is individually handled in a controlled manner from introduction until the coating or coatings are completely cured.

SUMMARY OF THE INVENTION

These and other objects of the present invention are achieved by apparatus comprising a plate and a plurality of tablet holders which may be selectively engaged with a plurality of vacuum tubes. The gentle attachment provided by the vacuum tubes permits the plate containing the product to be inverted and precisely dipped into a quantity of coating material in a controlled manner. The plate and tablet holders disclosed also permit the product to be inverted and placed in a second plate so that the uncoated portion residing against the vacuum tube may be coated. This feature also permits a second color or type of coating to be placed upon this portion of the product. Methods of coating products are also disclosed.

DETAILED DESCRIPTION OF THE PREFERRED EMBODIMENTS

Figure 1:
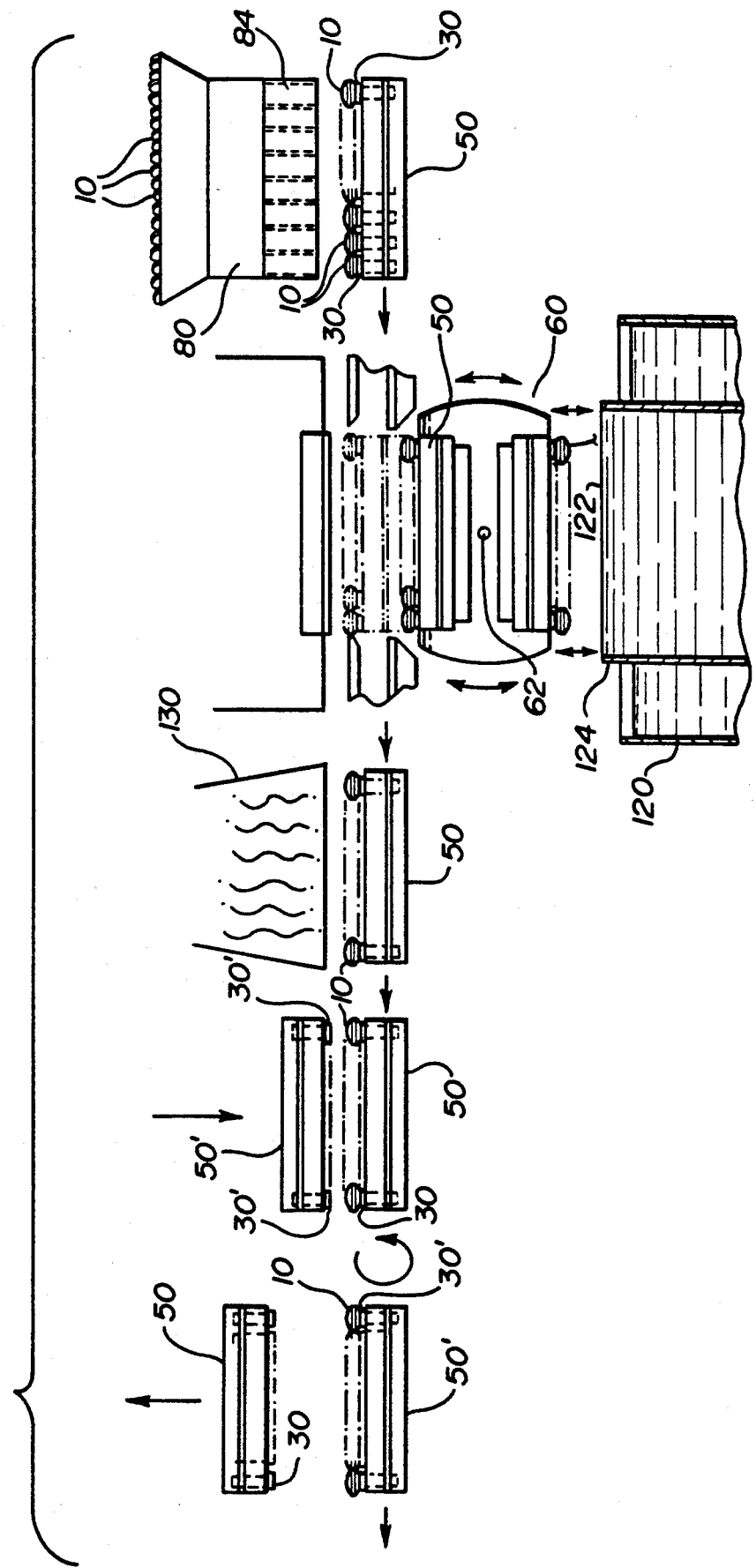
FIG. 1 is a partially diagrammatic, partially schematic representation of the coating apparatus of the present invention.

A generalized representation of the apparatus used in a preferred embodiment of the present invention is shown in FIG. 1. It will be understood that the descriptions set forth may be applied to numerous types and shapes of products. The type of tablet illustrated and the sequence shown are for purposes of explanation only.

A plurality of the product 10 to be coated is placed in a feeder means 80. Preferably, the feeder will be comprised of a hopper 82 and a series of feeder tubes 84 which align, orient and dispense the product 10 in the appropriate manner. Initially disposed directly beneath the feeder tubes 84 and in registration therewith is a plate 50. The plate 50 has a plurality of tablet holders 30 which, as explained below, restrain the product during certain portions of the coating process. The tablet holders 30 preferably correspond to the feeder tubes 84 and thus, most preferably, each tube 84 feeds a single product 10 into a single tablet holder 30.

Conveyor means transfer the plate 50 from the feeder 80 to the vacuum chamber 60. In a preferred embodiment shown in FIG. 1, the vacuum chamber 60 is adapted to receive and make vacuum tight connections with two plates 50. As shown by the arrows, the vacuum chamber 60 is further provided with manipulating means whereby it may be moved up and down, and rotated about a pivot point 62.

A first dipping tank 120 is disposed beneath the vacuum chamber 60 and is filled with a quantity of coating material. Preferably a coating material such as gelatin is used and, most preferably, the dipping tank 120 is provided with pumps and conduits whereby the coating material is continuously circulated. As illustrated, the dipping tank is most preferably constructed to form a meniscus surface 122 by pumping the coating material into an inner tank 124 which is permitted to overflow into the larger tank 120. Such a system prevents the coating material from hardening while the apparatus is in use and helps to ensure that the coating material presents the same even and substantially level surface to the product being dipped at all times.

In operation, the plate 50 is moved into engagement with the vacuum chamber 60 and then the chamber 60 and the plate 50 are rotated one-half revolution. As explained below, the vacuum chamber 60 creates a vacuum within the tablet holders 30 which holds the product 10 in place and in the correct orientation to be dipped. The vacuum chamber 60 is next lowered into dip tank 120 to a predetermined depth and then withdrawn. The vacuum chamber 60 is then rotated one and one-half revolutions in order to return the plate 50 to its original orientation. The additional full revolution beyond that required provides a dwell time, permitting the coating to initially "set" and also prevents the coating from running or sagging due to gravity by constantly reorienting the product 10. However, a rotation of as little as one-half of a revolution may be adequate in some instances. At this point, the plate 50 may be returned to the conveyor means and removed from the vacuum chamber 60.

The design of the vacuum chamber 60 and placement of the dip tank 120 illustrated permit a wide variety of coatings to be effectively and efficiently achieved. Although the dipping of a substantially cylindrical tablet having concave faces to form a coating having circumferential seam is illustrated, those of ordinary skill will understand that numerous other shapes of product, as well as other coating schemes are possible using the apparatus disclosed. As will be explained below, the shape of the tablet holders 30 and the design of the sub-components of the vacuum chamber 60 may be readily adapted for particular requirements. Also, as illustrated in FIG. 1, throughput may be increased by designing the vacuum chamber 60 to form a vacuum tight seal with further plates 50, such that each time the vacuum chamber 60 is rotated, a plate 50 which has already been lowered into the dipping tank 120 is returned to the conveyor means.

After the plate 50 containing the partially coated product 10 is removed from the vacuum chamber 60 the plate may be passed through a dryer means 130 for curing the coating material. As will be understood by those of ordinary skill, the dryer 130 will be chosen to correspond to the heat and moisture requirements of the coating material being used. Radiant heat, forced hot air, microwave dryers and combinations of these types are among the types available. Depending upon the type of dryer 130 chosen, one or more conveyors and other apparatus may be required to transfer the plates 50 into and out of the dryer 130.

After the coating has been cured, the plate 50 is again returned to conveyor means and is preferably transferred to another location. At this point, although only a portion of each individual product 10 has been coated, it may be desirable to eject the product 10 and consider the process complete. This may be true, for example, where the product has already been coated and the above-described process is carried out to add a second color to a portion of the product.

In a preferred embodiment, however, the present invention provides methods and apparatus which permit the uncoated portion of the product 10 to be coated. First, a second plate 50' is positioned in registration with the product contained on the first plate 50, as illustrated in FIG. 1. The second plate 50' is lowered until the coated side of the product 10 is disposed within the tablet holders 30' of the second plate 50'. The resulting "sandwich" of the first plate 50, the product 10 and the second plate 50' is then rotated one-half revolution by the conveyor/manipulator means. As shown, the positions of the plates 50,50' are thus reversed, and when the first plate 50 is removed the uncoated portion of the product 10 is exposed. The second plate 50' may then be transferred to the starting point of the dipping process and put through the sequence of manipulations necessary to form a coating which were set forth above using either the same apparatus or further apparatus, using either the same coating material or a different coating material.

In the instance where the same apparatus is used to place coating upon the uncoated portion of the product 10, the second plate 50' may be preferably conveyed or otherwise transported to a location just before the vacuum chamber 60, i.e., between the vacuum chamber 60 and the feeder 80 illustrated in FIG. 1. The second plate 50' would simply be inserted into engagement with the vacuum chamber 60 and the above described apparatus would carry out substantially the same sequence of functions in terms of dipping the product 10, curing the coating as needed, etc. After the product 10 has been fully coated and cured, it may be ejected prior to the transfer stage between the first and second plates 50,50'.

In another embodiment of the present invention, after the partially coated product has been transferred to the second plate 50', the plate 50' may enter a duplicate series of apparatus, such as that described above with reference to FIG. 1. In other words, a second vacuum chamber, dipping tank, dryer, and manipulating and conveying apparatus may be provided. After the product 10 is coated and cured using this second set of apparatus, the completed product is ejected.

Figure 2:
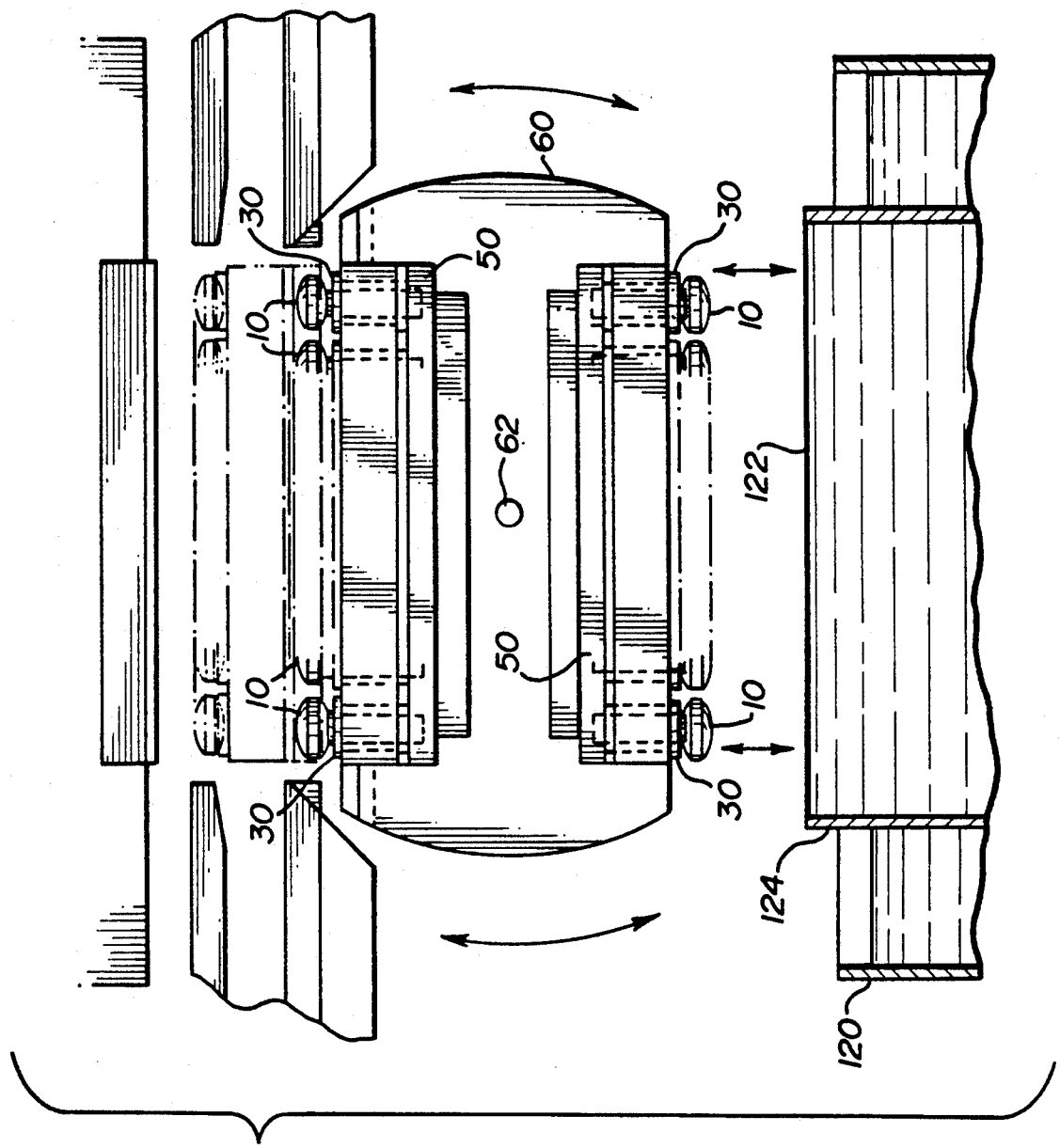
FIG. 2 is a broken away, partially cross-sectioned side view of a portion of the apparatus of FIG. 1.

Referring now to FIG. 2, a more detailed view of the vacuum chamber 60 described above is shown. As explained above, in a preferred embodiment two plates 50 (or 50') are retained in a vacuum tight seal upon the vacuum chamber 60, thereby permitting more efficient indexing between the raising and lowering of the apparatus and the infeed and outfeed of the plates 50 from the vacuum chamber 60.

As shown, the entire chamber may be raised or lowered to bring the product 10 into contact with the surface of the coating material 122. The vertical motion also preferably provides a transfer between the vacuum chamber 60 and the manipulating means, as shown in phantom in FIG. 2. This latter vertical movement also provides clearance when the vacuum chamber 60 is rotated during the dipping process explained above with reference to FIG. 1.

Figure 3:
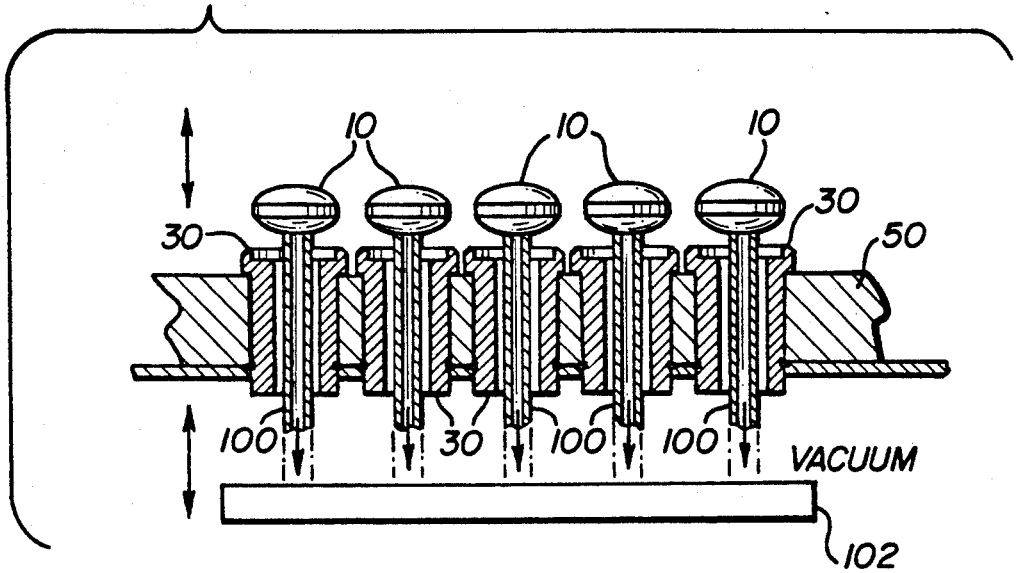
FIG. 3 depicts a cross-sectional view of the tablet holders and plate used in a preferred embodiment of the present invention.

Further details of the vacuum chamber 60 are shown in FIG. 3, which illustrates broken-away section of the plate 50 and the vacuum chamber 60. As seen in cross-section, the plate 50 has a plurality of tablet holders 30 inserted into a series of openings. The plate 50 rests upon the vacuum chamber 60 and forms a seal therewith. A plurality of vacuum tubes 100 extend through the tablet holders 30 and, when in use, engage and slightly lift the product 10 from the tablet holders 30 as shown. The vacuum created within the vacuum chamber 60 is channeled through the vacuum tubes 100 by a manifold or similar means, thereby permitting the vacuum to act upon the surface of the product 10 when contacted by the vacuum tubes 100. By providing vacuum tube actuator means 102 for raising and lowering the vacuum tubes 100 relative to the vacuum chamber 60, the vacuum tubes may be selectively placed in the raised position illustrated. The actuator 102 may be a common bar or mounting structure which is moved by a gear, cam or pulley system.

When in the position illustrated, it is possible to invert or otherwise manipulate the product 10 as described above without friction or the use or mechanically actuated clamps. The vacuum handling system disclosed by the present invention provides a secure retention of the product while minimizing the possibility of damaging either the coating or the product 10 itself. As explained above, the methods and apparatus of the present invention are useful for numerous shapes and sizes of product 10, however, most preferably, the product 10 will have one or more curved surfaces, as illustrated. The curved surfaces permit the tubes 100 to be made from a rigid material such as stainless steel. Those of ordinary skill will realize however, that nearly any shape and any orientation of product may be retained using appropriately designed vacuum tubes. Finally, in certain instances it will be desirable to provide a cushion or resilient tip on the distal end of the vacuum tube in order to ensure a sufficient grip.

Figure 4:
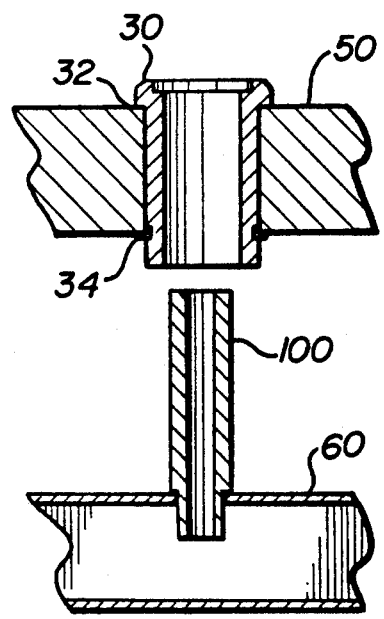
FIG. 4 is a broken away cross-sectional view of the plate of FIG. 3, illustrating the tablet holder and vacuum tube used in a preferred embodiment of the present invention.

Referring now to FIG. 4, a preferred embodiment of the tablet holder 30 is illustrated. A shoulder 32 is formed at a first end of the tablet holder to provide a positive stop. A groove is formed at a second end, into which an "O" ring or the like may be engaged to retain the tablet holder 30 in the plate 50. As will be understood by those of ordinary skill, the tablet holder 30 end the plate 50 may be in certain instances formed as an integral component. FIG. 4 also illustrates the vacuum tube 100 in the withdrawn position. When the vacuum tube 100 is in the withdrawn position, the depression formed in the tablet holder 30 is the only means for restraining the product 10 (not shown in FIG. 4).

The present invention also provides methods for coating a product 10 in accordance with the present invention. A preferred embodiment of the methods of the present invention is illustrated by the sequence of views in FIG. 5. For purposes of illustration and explanation a single product 10, vacuum tube 100 and tablet holder 30 are illustrated, along with broken away portions of other apparatus such as the plate 50. As shown in the upper left section of FIG. 1, a plate 50 containing a tablet holder 30 is positioned beneath the feeder means 80 for feeding a tablet described above and a product 10 is disposed within the tablet holder 30. Next, the plate 50 containing the individual products 10 is moved into the vicinity of the vacuum chamber 60, where it is cleaned of dust and particulate matter. For clarity, the representation of the vacuum chamber 60 is omitted from the other views shown in FIG. 5. An individual vacuum tube 100 is then brought into position and placed in close proximity or contact with the product 10. At this point, the vacuum created within the vacuum tube 100 "picks up" or engages the product 10. After the individual products 10 have been engaged by the vacuum tubes 100, the entire plate 50 is rotated one-half of a revolution, suspending the product 10 by the vacuum tube 100. The vacuum tube 100 and the product 10 attached thereto may now be moved into position and lowered into a coating tank 120. The depth to which the product 10 is lowered is a function of the motion of the vacuum tubes 100 and plate 50, which may be precisely regulated by hydraulic actuators, gear trains or other means for actuating the vacuum tube 100 and/or moving the plate 50. The vacuum tube 100 and the partially coated product 10 are then withdrawn from the coating tank 120, but the product 10 is not fully withdrawn into its holder 30. Instead, the plate 50 and partially extended vacuum tubes 100 are rotated one and one-half revolutions, returning the plate 50 to its initial orientation. The additional revolution provides a dwell, permitting the coating to initially set, as well as aiding in the provided evenness of the coating by preventing the coating from running due to gravity. In certain embodiments, however, this dwell may be unnecessary and the plate need only be rotated one-half of a revolution. After the plate 50 has been returned to its initial position, the vacuum tube 100 may be withdrawn until the product 10 again rests in a holder 30 within the plate 50. Once the vacuum tube 100 has been sufficiently withdrawn, the vacuum connection to the product 10 is broken and gravity and the holder 30 restrain the product 10.

Figure 5:
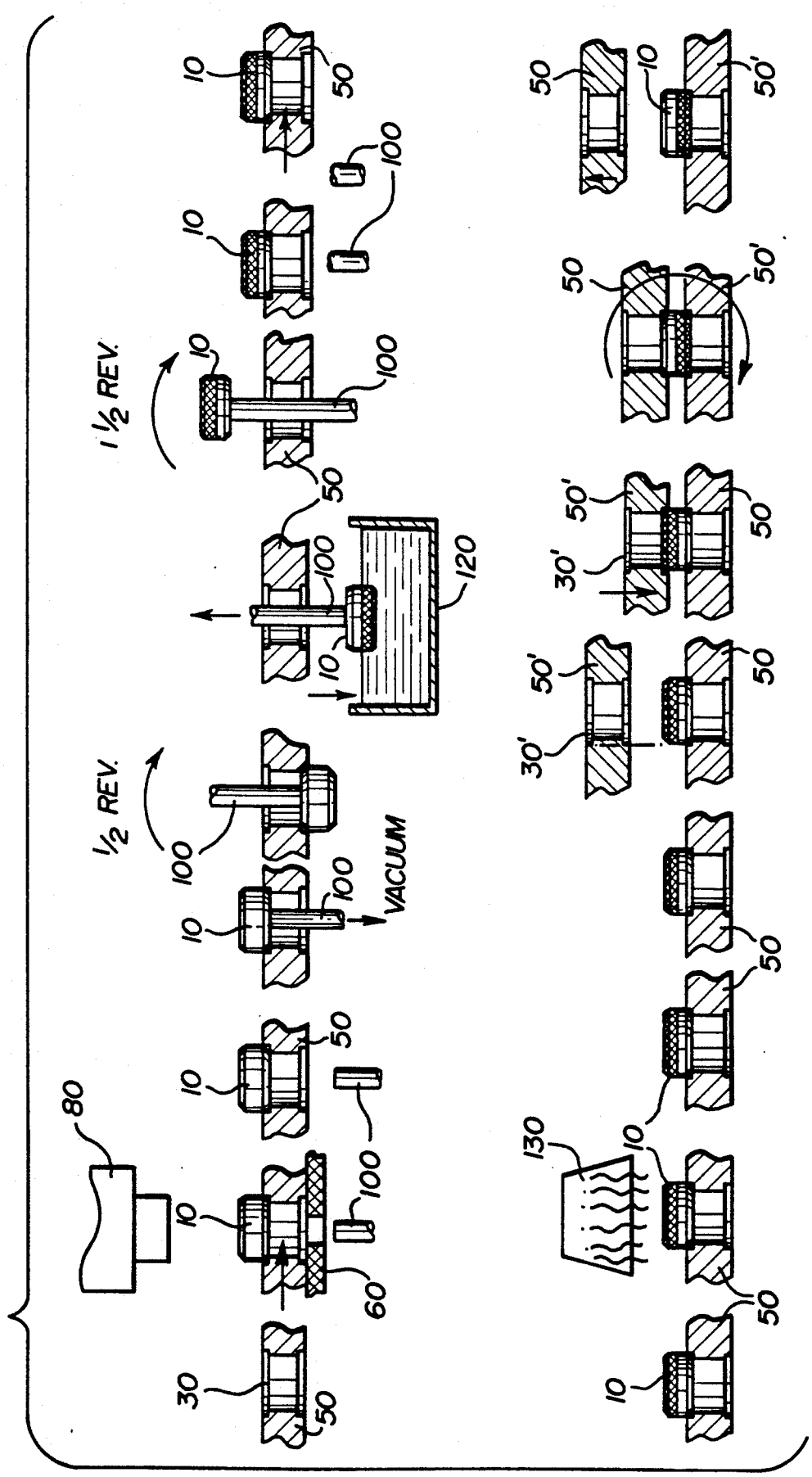
FIG. 5 is a partially diagrammatic, partially schematic representation of the steps of a preferred method for coating a tablet in accordance with the present invention.

As shown at the lower left portion of FIG. 5, once the individual products 10 have been released from the effect of the vacuum, the plate 50 bearing the partially coated individual products 10 may be moved into a dryer 130. Using conveyors or other conventional means, the plates are pushed into the dryer 130 and dried. After the coating has cured and the plates 50 have exited the dryer 130, a second plate 50' is moved into position such that the tablet holders 30' in the second plate 50' are in registry with the tablet holders 30 in the first plate 50, which contain the partially coated product 10. The second plate 50' is lowered toward the first plate 50 until the tablet holders 30' in the second plate 50' have engaged the product held in the first plate 50. Thus, as illustrated, the product 10 is "sandwiched" between the first and second plates 50,50'. The pair of plates 50, 50' are then rotated one-half revolution, thereby reversing the relative positions of the first and second plates 50,50'. The first plate 50 is then raised, leaving the uncoated portion of the product 10 on the top, exposed, and the coated side on the bottom, i.e., within the tablet holder 30 of the plate 50'.

At this point, the preferred embodiment of the method illustrated has completely coated and cured a coating on about one-half of the product 10. It will be understood, however, that the above-described method may be repeated by transferring the plate 50' shown in the lower right section of the illustration to the upper left section, in other words, to the beginning of the process at the point immediately after the individual products 10 have been loaded into the plates 50. In this embodiment of the present invention, the above-described process is repeated and the remainder of the product 10 is coated. It should be further understood, however, that in any event, more or less than one-half of the tablet may be coated to provide different overall coating effects. For instance, if both "passes" coated less than one-half the height of the tablet, a band of uncoated product would remain exposed. On the other hand, if one or both of the "passes" were carried out to a depth substantially greater than one-half the height of the tablet, an overlapped "seam" appearance would be created.

Figure 6:
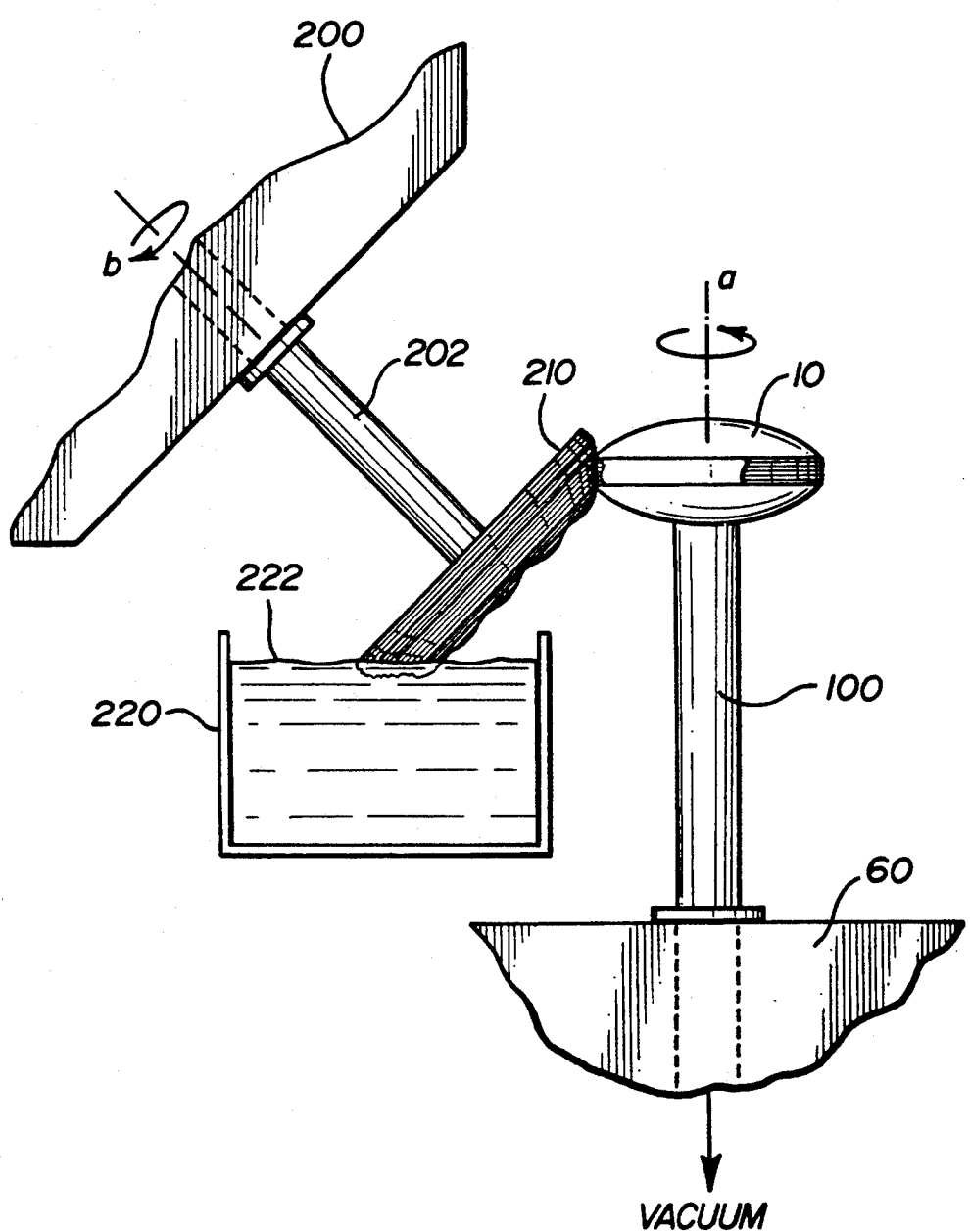
FIG. 6 depicts another embodiment illustrating the tablet being coated by a rotating applicator.

Referring now to FIG. 6, another feature of certain embodiments of the present invention is illustrated. In these embodiments, the vacuum tube 100 will be constructed such that it may be rotated about its longitudinal axis as shown by arrow a in FIG. 6. As understood by those of ordinary skill, such rotation may be accomplished using gear trains, belts and pulleys or other means for transferring rotational motion to a shaft.

While rotating, the vacuum tube 100 is also acted upon by a source of vacuum, either the vacuum chamber 60 discussed above, or another source. The product 10 is thus firmly held in place upon the rotating vacuum tube 100 as shown. While the product 10 is rotating, it is brought into contact with a rotating wheel 210 or other application means for applying a coating. Preferably, the rotating wheel 210 provided is shaped and manipulated so as to come into close proximity with a portion of the product 10, such as the central "edge" shown. As the wheel 210 and product 10 rotate, the wheel 210 also passes through a quantity of coating material 222 and precisely coats a portion of the product 10. The wheel 210 rotates about a shaft 202 in the direction shown by arrow b and is mounted on a support structure 200 at an appropriate angle.

The present invention therefore also discloses methods whereby a relatively narrow stripe or band of coating material may be applied to a product. Most preferably, the product and the means for applying the coating rotate and are placed in close proximity. The means for applying the coating is preferably at least partially immersed in a quantity of coating material and passes therethrough while rotating. Using the embodiments illustrated in FIG. 6, it is possible not only to provide a different color "band" or stripe, but to also increase the thickness of the coating in a specified section, thereby creating the appearance of a seam or an overlapped gelatin capsule.

Although certain embodiments of the methods and apparatus of the present invention have been described above with particularity, these examples are for purposes of illustration and are not limiting. Numerous variations and adaptations of the principles of the present invention will immediately present themselves to those of ordinary skill. Accordingly, reference should be made to the appended claims to ascertain the scope of the present invention.

What is claimed is:

1. Apparatus for applying a coating to a tablet product comprising:
   a first plate having a one or more tablet holder means for retaining the tablet product, said tablet holder means having communication means for receiving one or more vacuum tubes;
   a vacuum chamber means connected to a source of vacuum;
   one or more vacuum tubes disposed within said vacuum chamber and connected to said vacuum source for communicating vacuum forces to said tablet holder means;
   vacuum tube actuator means for raising and lowering said vacuum tubes relative to said vacuum chamber between an actuated position extending from said tablet holder means for retaining said tablet product on the ends of said tubes extending from said tablet holder, and an unactuated position;
   one or more conveyor means for manipulating said plate to position said plate adjacent said vacuum chamber means;
   dip station means for raising and lowering said plate to contact said tablet product with coating material contained in a dip tank means; and
   dip tank means for retaining a quantity of coating material.

2. The apparatus of claim 1, wherein said plate and said tablet holders are formed as an integral assembly.

3. The apparatus of claim 1, wherein said plate comprises a plurality of individual tablet holders and a plate adapted to retain said individual tablet holders.

4. The apparatus of claim 3, wherein said individual tablet holders comprise a substantially cylindrical portion having two ends and, a shoulder portion formed at a first end and a circumferential groove formed at a second end.

5. The apparatus of claim 1, wherein said vacuum chamber means is adapted to engage said plate to form a vacuum tight seal therebetween.

6. The apparatus of claim 5, wherein said vacuum chamber is further adapted to engage a second plate and form a vacuum tight seat therewith.

7. The apparatus of claim 6, wherein said vacuum chamber is mounted to shaft means for selectively rotating said vacuum chamber and said first and second plates.

8. The apparatus of claim 1, wherein said dip tank means is adapted to hold coating material that is comprised of a gelatinous material.

9. The apparatus of claim 1, wherein said dip tank means comprises means for circulating said coating material.

10. The apparatus of claim 1, further comprising feeder means for orienting and disposing one or more of said tablet product in said tablet holders.

11. The apparatus of claim 10, wherein said feeder means comprises one or more feeder tubes and means for positioning said tubes in registration with said tablet holders.

12. The apparatus of claim 1, further comprising dryer means for curing said coating material after it is applied to said tablet product.

13. The apparatus of claim 1, further comprising means for ejecting said product from said plates after said dip station.

14. The apparatus of claim 1, further comprising:
a second plate means having a number of tablet holder means corresponding to the tablet holder means of the first plate;
at least a second conveyor means for manipulating said second plate means into registration with said first plate means aligning the respective tablet holder means;
means for rotating said first and second plate means while they are in registration.

15. The apparatus of claim 14, further comprising conveyor means for transporting said second plate to said vacuum chamber means.

16. The apparatus of claim 14, further comprising:
a second vacuum chamber means connected to a source of vacuum;
a further plurality of vacuum tubes disposed within said second vacuum chamber and connected to said vacuum source for receipt by the tablet holder means;
second vacuum tube actuator means for raising and lowering said vacuum second tubes relative to said second vacuum chamber between an actuated position extending from said tablet holder means for retaining said tablet product on the ends of said second tubes extending from said tablet holder, and an unactuated position;
conveyor means for manipulating said second plate adjacent said second vacuum chamber means;
second dip station means for raising and lowering said second plate to contact said tablet product with coating material in a second dip tank means; and
second dip tank means for retaining a quantity of coating material.

17. The apparatus of claim 1, wherein said vacuum chamber is mounted to shaft means for selectively rotating said vacuum chamber and said plate.

18. The apparatus of claim 1, wherein said vacuum tube actuator means further comprises means for rotating one or more of said vacuum tubes about its longitudinal axis.

19. The apparatus of claim 18 further comprising rotating means for applying a further coating to said tablet product after applying said coating material.

20. The apparatus of claim 19 wherein said rotating means comprises a wheel at least partially immersed in a quantity of a coating material.

* * * * *